United States Patent [19]
Ditzel et al.

[11] Patent Number: 5,877,347
[45] Date of Patent: Mar. 2, 1999

[54] IRIDIUM CATALYZED CARBONYLATION PROCESS FOR THE PRODUCTION OF ACETIC ACID

[75] Inventors: Evert Jan Ditzel, Howden nr Goole; John Glenn Sunley, Cottingham; Robert John Watt, Beverley, all of United Kingdom

[73] Assignee: BP Chemicals Limited, London, England

[21] Appl. No.: 992,103

[22] Filed: Dec. 17, 1997

[30] Foreign Application Priority Data

Dec. 19, 1996 [GB] United Kingdom .................. 9262317

[51] Int. Cl.⁶ ........................... C07C 51/12; C07C 51/10
[52] U.S. Cl. ............................. 562/519; 562/520
[58] Field of Search ..................... 562/519, 520

[56] References Cited

U.S. PATENT DOCUMENTS 5,510,524   4/1996  Garland et al. .

FOREIGN PATENT DOCUMENTS

| | | |
|---|---|---|
| 0 567 331 A2 | 10/1993 | European Pat. Off. . |
| 616 997 A1 | 9/1994 | European Pat. Off. . |
| 0 618 184 A1 | 10/1994 | European Pat. Off. . |
| 0 643 034 A1 | 3/1995 | European Pat. Off. . |
| 0 728 727 A1 | 8/1996 | European Pat. Off. . |
| 0 752 406 A1 | 1/1997 | European Pat. Off. . |

*Primary Examiner*—Gary Geist
*Assistant Examiner*—Rosalynd Keys
*Attorney, Agent, or Firm*—Nixon & Vanderhye

[57] ABSTRACT

A process for the production of acetic acid comprises (1) continuously feeding methanol and/or a reactive derivative thereof and carbon monoxide to a carbonylation reactor containing a liquid reaction composition comprising an iridium carbonylation catalyst, methyl iodide co-catalyst, a finite concentration of water, acetic acid, methyl acetate and, optionally at least one promoter, (2) carbonylating the methanol and/or reactive derivative thereof with the carbon monoxide in the liquid reaction composition to produce acetic acid; and (3) recovering acetic acid from the liquid reaction composition, there being continuously maintained (a) in the liquid reaction composition water at a concentration of no greater than 4.5% by weight, and (b) in the reactor a carbon monoxide partial pressure in the range from greater than 0 to 7.5 bar.

16 Claims, 6 Drawing Sheets

FIG. 6 Propionic acid production for Ir/Ru catalysed reactions

IRIDIUM CATALYZED CARBONYLATION PROCESS FOR THE PRODUCTION OF ACETIC ACID

The present invention relates to a process for the production of acetic acid and in particular to a process for the production of acetic acid by carbonylation in the presence of an iridium catalyst and methyl iodide co-catalyst.

Preparation of carboxylic acids by iridium-catalyzed carbonylation processes is known and is described, for example in GB-A-1234121, U.S. Pat. No. 3,772,380, DE-A-1767150, EP-A-0616997, EP-A-0618184, EP-A-0618183 and EP-A-0657386.

EP-A-0618184 describes a carbonylation process for the production of carboxylic acids and/or their esters in the presence of an iridium catalyst. The reaction composition is characterized as comprising between 0 exclusive and 10% water; between 0 exclusive and10% halogenated co-catalyst; between 2 and 40% ester and carboxylic acid solvent. The total pressure is stated to be in the range generally between 5 and 200 bar and more particularly between 5 and 100 bar whilst all the Examples were performed at 30 bar.

EP-A-0643034 describes a process for the carbonylation of methanol an/or a reactive derivative thereof in the presence of acetic acid, an iridium catalyst, methyl iodide, at least a finite concentration of water, methyl acetate and a promoter selected from ruthenium and osmium. Batch and continuous experiments are described therein. In the continuous experiments the water concentration is as low as 6.8% by weight.

Our unpublished European Patent Application No. 96302734.7 filed on 18 Apr. 4, 1996 discloses a process for the production of acetic acid comprising (1) continuously feeding methanol and/or a reactive derivative thereof and carbon monoxide to a carbonylation reactor which contains a liquid reaction composition concentration of water, acetic acid, methyl acetate and at least one promoter; (2) contacting the methanol and/or reactive derivative thereof with the carbon monoxide in the liquid reaction composition to produce acetic acid; and (3) recovering acetic acid from the liquid reaction composition characterized in that there is continuously maintained in the liquid reaction composition throughout the course of the reaction (a) water at a concentration of no greater than 6.5% by weight, (b) methyl acetate at a concentration in the range 1 to 35% by weight and (c) methyl iodide at a concentration in the range 4 to 20% by weight.

The carbon monoxide partial pressures in European Patent Application No. 96302734.7 are said to be in the range 1–70 bar preferably 1 to 35 bar, more preferably 1 to 15 bar. Total pressures are in the range 10 to 200 bar, preferably 15 to 100 bar, more preferably 15 to 50 bar. All the batch carbonylation experiments reported were carried out at 28 barg total pressure and the continuous experiments were carried out at 24 to 30 barg total pressure.

There remains a need for an improved iridium-catalysed carbonylation process.

We have now found that the carbon monoxide partial pressure has a significant effect upon the carbonylation reaction rate, depending upon the water concentration in the liquid reaction composition. Under high water conditions (greater than 5%) by weight water at 30% by weight methyl acetate) using an unpromoted iridium catalyst increasing the total pressure from 16.5 to 22 bar (estimated CO partial pressures of greater than 0 to 6 bare respectively) results in an increase in the reaction rate, whereas under low water conditions, for example 1% by weight, decreasing the total pressure from 22 to 16.4 (estimated CO partial pressures of 6 to greater than 0 bar respectively) increases the reaction rate. A similar trend is also observed for data at 15% by weight methyl acetate and the data from ruthenium promoted iridium catalysts. To express the foregoing observations in an alternative manner, the position of the rate maxima in a graph of carbonylation rate versus water concentration moves to lower water concentrations as the carbon monoxide partial pressure is reduced.

Accordingly the present invention provides a process for the production of acetic acid which process comprises (1) continuously feeding methanol and/or a reactive derivative thereof and carbon monoxide to a carbonylation reactor containing a liquid reaction composition comprising an iridium carbonylation catalyst, methyl iodide co-catalyst, a finite concentration of water, acetic acid, methyl acetate and, optionally at least one promoter; (2) carbonylating the methanol and/or reactive derivative thereof with the carbon monoxide in the liquid reaction composition to produce acetic acid; and (3) recovering acetic acid from the liquid reaction composition, there being continuously maintained (a) in the liquid reaction composition water at a concentration of no greater than 4.5% by weight, and (b) in the reactor a carbon monoxide partial pressure in the range from greater than 0 to 7.5 bar.

The present invention solves the technical problem defined above by continuously maintaining a defined carbon monoxide partial pressure and a liquid reaction composition having a defined water concentration. This provides several technical advantages.

Thus in the present invention the position of the rate maxima moves towards lower water concentrations as the carbon monoxide partial pressure is reduced. The use of low carbon monoxide partial pressures also leads to the advantage that the production of by-products, e.g. propionic acid and its precursors, is also reduced.

Also, in the process of the present invention, by operating at a water concentration of no (greater than 4.5% by weight, recovery of acetic acid from the reaction composition withdrawn from the carbonylation reactor is facilitated because the amount of water which has to be separated from the acetic acid is reduced; separation of water from the acetic acid is an energy-intensive part of the recovery process and reduced water concentration results in reduced processing difficulty and/or costs.

The increased carbonylation rate at the low water concentration of the present invention may allow operation at a reduced iridium catalyst concentration whilst maintaining the rate of carbonylation. This has benefits of reduced production rate of by-products such as propionic acid.

Water may be formed in situ in the liquid reaction composition, for example, by the esterification reaction methanol reactant and acetic acid product. Small amounts of water may also be produced by hydrogenation of methanol to produce methane and water. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. The water concentration in the liquid reaction composition is no greater than 4.5% by weight that is, less than or equal to 4.5% by weight and preferably no greater than 3% by weight. The water concentration is preferably at least 0.1% by weight, more preferably at least 0.5% by weight.

In the process of the present invention, suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants. If methyl acetate or dimethyl ether are used, water co-reactant is required to produce acetic acid. At least some of the methanol and/or reactive derivative thereof will be converted to, and hence present as, methyl acetate in the liquid reaction composition by reaction with acetic acid product or solvent. In the process of the present invention the concentration of methyl acetate in the liquid reaction composition is suitably in the range 1 to 70% by weight, preferably 2 to 50% by weight, preferably 5 to 50% by weight, preferably 5 to 40% by weight, more preferably 10 to 40% by weight.

In the process of the present invention, the concentration of methyl iodide co-catalyst in the liquid reaction composition is preferably in the range 1 to 20% by weight, more preferably 4 to 16% by weight. As the methyl iodide co-catalyst concentration is increased, the rate of production of by-products such as propionic acid, carbon dioxide and methane is generally reduced. Also, as the concentration of methyl iodide is increased, phase separation of aqueous and methyl iodide phases in the acetic acid recovery stage may be facilitated.

In the process of the present invention, the iridium carbonylation catalyst is preferably present in the liquid reaction composition at a concentration in the range 400 to 5000 ppm measured as iridium, more preferably in the range 500 to 3000 ppm measured as iridium, yet more preferably in the range 700 to 3000 ppm measured as iridium. In the process of the present invention, the rate of the carbonylation reaction increases as the concentration of iridium is increased.

The iridium catalyst in the liquid reaction composition may comprise any iridium containing compound which is soluble in the liquid reaction composition. The iridium cayalyst may be added to the liquid reaction composition for the carbonylation reaction in any suitable form which dissolves in the liquid reaction composition or is convertible to a soluble form which. Examples of suitable iridium-containing compounds which may be added to the liquid reaction composition include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $IrO_2$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$, preferably, chloride-free complexes of iridium such as acetates, oxalates and acetoacetates which are soluble in one or more of the carbonylation reaction components such as water, alcohol and/or carboxylic acid. Particularly preferred is green iridium acetate which may be used in an acetic acid or aqueous acetic acid solution.

In the process of the present invention at least one promoter is optionally present in the reaction composition. Suitable promoters are preferably selected from ruthenium, osmium, rhenium, tungsten, zinc, cadmium, indium, gallium and mercury, and are more preferably selected from ruthenium and osmium. Ruthenium is the most preferred promoter. Preferably, the promoter is present in an effective amount up to the limit of its solubility in the liquid reaction composition and/or any liquid process streams recycled to the carbonylation reactor from the acetic acid recovery stage. The promoter is suitably present in the liquid reaction composition at a molar ratio of promoter iridium of [0.5 to 15]:

1. A suitable promoter concentration is 400 to 5000 ppm.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form. Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $[Ru(CO)_2I_2]_n$, $[Ru(CO)_4I_2]$, $[Ru(CO)_3I_2]_2$, tetra(aceto)chlororuthenium(II,III), ruthenium (III) acetate, ruthenium (III) propionate, ruthenium (III) butyrate, ruthenium pentacarbonyl, triruthenium dodecacarbonly and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetrachlorobis(benzene)diruthenium(II), dichloro(cyclocta-1,5-diene)ruthenium(II)polymer and tris(acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^-H^+$, petachloro-$\mu$-nitrodiosmium and mixed osmium halocarbonyls such as tricarbonyldichloroosmium (II) dimer and other organoosmium complexes.

Examples of suitable rhenium-containing compounds which may be used as sources of promoter include $Re_2(CO)_{10}$, $Re(CO)_5Cl$, $Re(CO)_5BR$, $Re(CO)_5I$, $ReCl_3.xH_2O$, $[Re(CO)_4I]_2$, $[Re(CO)_4I_2]^-H^+$ and $ReCl_5.yH_2O$.

Examples of suitable tungsten-containing compounds which may be used as sources of promoter include $W(CO)_6$, $WCl_4$, $WCl_6$, $WBr_5$, $WI_2$, or $C_9H_{12}$ $W(CO)_3$ and any tungsten chloro-bromo- or iodo-carbonyl compound.

Examples of suitable cadmium-containing compounds which may be used include $Cd(OAc)_2$, $CdI_2$, $CdBr_2$, $CdCl_2$, $Cd(OH)_2$, and cadium acetylacetonate.

Examples suitable mercury-containing compounds which may be used as sources of promoter include $Hg(OAc)_2$, $HgI_2$, $HgCl_2$, $HgCl_2$, $Hg_2I_2$, and $Hg_2Cl_2$.

Examples of suitable zinc-containing compounds which may be used as sources of promoter includes $Zn(OAc)_2$, $Zn(OH)_2$, $ZnI_2$, $ZnBr_2$, $ZnCl_2$ and zinc acetylacetonate.

Examples of suitable gallium-containing compounds which may be used as sources of promoter include gallium acetylacetoneate, gallium acetate, $GaCl_3$, $GaBr_3$, $GaI_3$, $Ga_2Cl_4$ and $Ga(OG)_3$.

Examples of suitable indium-containing compounds which may be used as sources of promoter include indium acetylacetonate, indium acetate, $InCl_3$, $IbBr_3$, $InI_3$, $InI$ and $InI(OH)_3$.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide feed and generated in situ by the water gas shift reaction is preferably kept low as its presence may result in the formation of hydrogenation products. Thus, the amount of hydrogen in the carbon monoxide reactant is preferably less than 1 mol %, more preferably less than 0.5 mol % and yet more preferably less than 0.3 mol % and/or the partial pressure of hydrogen in the carbonylation reactor is preferably less than 1 bar partial pressure, more preferably less than 0.5 bar and yet more preferably less than 0.3 bar. The partial pressure of carbon monoxide in the reactor is in the range greater than 0 to 7.5 bar, typically from about 0.6 bar to 7.5 bar.

The total pressure of the carlbonylation reaction is suitably in the range 10 to 200 barg, preferably 15 to 100 barg, more preferably 15 to 50 barg. The temperature of the carbonylation reaction is suitably in the range 100° to 300° C., preferably in the range 150° to 220° C.

The process of the present invention is performed as a continuous process.

The acetic acid product may be recovered from the liquid reaction composition by withdrawing vapour and/or liquid from the carbonylation reactor and recovering acetic acid from the withdrawn material. Preferably, acetic acid is recovered from the liquid reaction composition by continuously withdrawing liquid reaction composition from the carbonylation reactor and recovering acetic acid from the withdrawn liquid reaction composition by one or more flash and/or fractional distillation stages in which the acetic acid is separated from the other components of the liquid reaction composition such as iridium catalyst, methyl iodide co-catalyst, promoter if present, methyl acetate, unreacted methanol, water and acetic acid solvent which may be recycled to the reactor to maintain their concentrations in the liquid reaction composition. To maintain stability of the iridium catalyst during the acetic acid product recovery stage, water in process streams containing iridium carbonylation catalyst for recycle to the carbonylation reactor should be maintained at a cencentration of at least 0.5% by weight.

A particularly preferred liquid reaction composition comprises about 0.5 to 2.5% by weight water, about 8% by weight methyl iodide co-catalyst, about 15% by weight methyl acetate, iridium catalyst at a concentration in the range 400 to 3000 ppm measured as iridium to give a rate of carbonylation reaction in the range of 5 to 40 mol/l/hr at a carbonylation reaction temperature of about 190° C. and a carbonylation reaction pressure of 16 to 24 barg and carbon monoxide partial pressure of greater than 0 to 7.5 bar, ruthenium promoter at a concentration in the range 400 to 4000 ppm measured as ruthenium to give a molar ratio of ruthenium:iridium of approximately [2.0 to 2.5]:1 and the balance of the reaction composition comprising substantially acetic acid. Higher or lower concentrations of catalyst and/or higher or lower temperatures and/or lower partial pressures of carbon monoxide may be used to obtain higher or lower rates of reaction.

The invention will now be illustrated by way of reference to the following experiments which are not according to the present invention because they are batch experiments, as opposed to continuous. Nevertheless the batch experiments provide a reasonable expectation of what might happen in a continuous process. Those experiments in which the water concentration is greater than 4.5% by weight and/or the carbon monoxide partial pressure is not in the range from greater than 0 to 7.5 bar are included only for the purpose of comparison.

BRIEF DESCRIPTION OF DRAWINGS

The data is presented in FIGS. 1 to 6 in which.

In the experiments at a total pressure of 16 barg we estimate that the CO partial pressure would be approximately zero. At higher total reaction pressure the CO partial pressures rise correspondingly depending upon the liquid composition up to a total reactor pressure of 24 barg which is estimated to correspond to approximately 7.5 bare partial pressure CO.

In the experiments reaction rates are quoted as number of moles of product/reactant produced/consumed per liter of cold degassed reactor composition per hour (mol/(l. hr)).

In the experiments the concentration of components and in particular of water and methyl acetate, during the carbonylation reaction was calculated from the starting composition, assuming the one mole of water is consumed for every mole of carbon monoxide that is consumed. No allowance was made for the organic components in the autoclave headspace.

Experimental Method

A 300 ml Hastelloy B2 autoclave equipped with a magnetically driven stirrer with gas dispersion impellers, a ballast vessel and a liquid catalyst injection system was used for a series of batch carbonylation experiments. A gas supply to the autoclave provided from a gas ballast vessel, feed gas being provided to maintain the autoclave at a constant pressure and the rate of gas uptake being calculated (with an accuracy believed to be ±1%) from the rate at which the pressure falls in the ballast vessel.

At the end of the experiment liquid and gas samples from the autoclave were analysed by gas chromatography.

For each batch carbonylation experiment the autoclave was charged with typically 10 g of acetic acid. For Ru promoted reactions the solid ruthenium promoter was also charged at this stage. The autoclave was then sealed and flushed three times with carbon monoxide. After this the main liquid charge (water, methyl acetate, acetic acid and methyl iodide was added to the autoclave via a funnel. The autoclave was then pressurized with carbon monoxide to a suitable pressure (see Table A) and heated with stirring (1500 r.p.m.) to 190° C. Once stable at this temperature a small amount of carbon monoxide was fed forward from the ballast vessel to give a suitable pressure (see Table A) The catalyst solution consisting of ca. 1.30 g of a water solution of $H_2IrCl_6$ dissolved in acetic acid and water was then added from the injection vessel using an overpressure of carbon monoxide. The overpressure (see Table A) was such that after injection the desired reaction pressure was attained. After catalyst injection the autoclave pressure was kept constant (±0.5 barg) using carbon monoxide fed from the ballast vessel.

After gas uptake from the ballast vessel had ceased (i.e. no gas consumed from the ballast vessel for 6 minutes) the autoclave was isolated from the gas supply and the reactor contents cooled to room temperature. The autoclave was vented and the vent gases sampled and analysed. The liquid reaction composition was discharged from the autoclave, sampled and was analyzed for liquid products and by-products.

TABLE A

| Reaction Pressure (barg) | 16 | 18 | 22 | 28 |
|---|---|---|---|---|
| Room Temperature Pressure (barg) | 0.5 | 1.3 | 3 | 6.5 |
| Pressure at 190° C. (barg) | 10 | 12 | 16 | 22 |
| Catalyst Injection Overpressure (barg) | 26 | 26 | 34 | 40 |

Component charges are given in Table 1. Reaction rates at 30% methyl acetate and 15% methyl acetate in the reaction composition and selectively to propionic acid precursor are given in Table 2.

Figure 1:
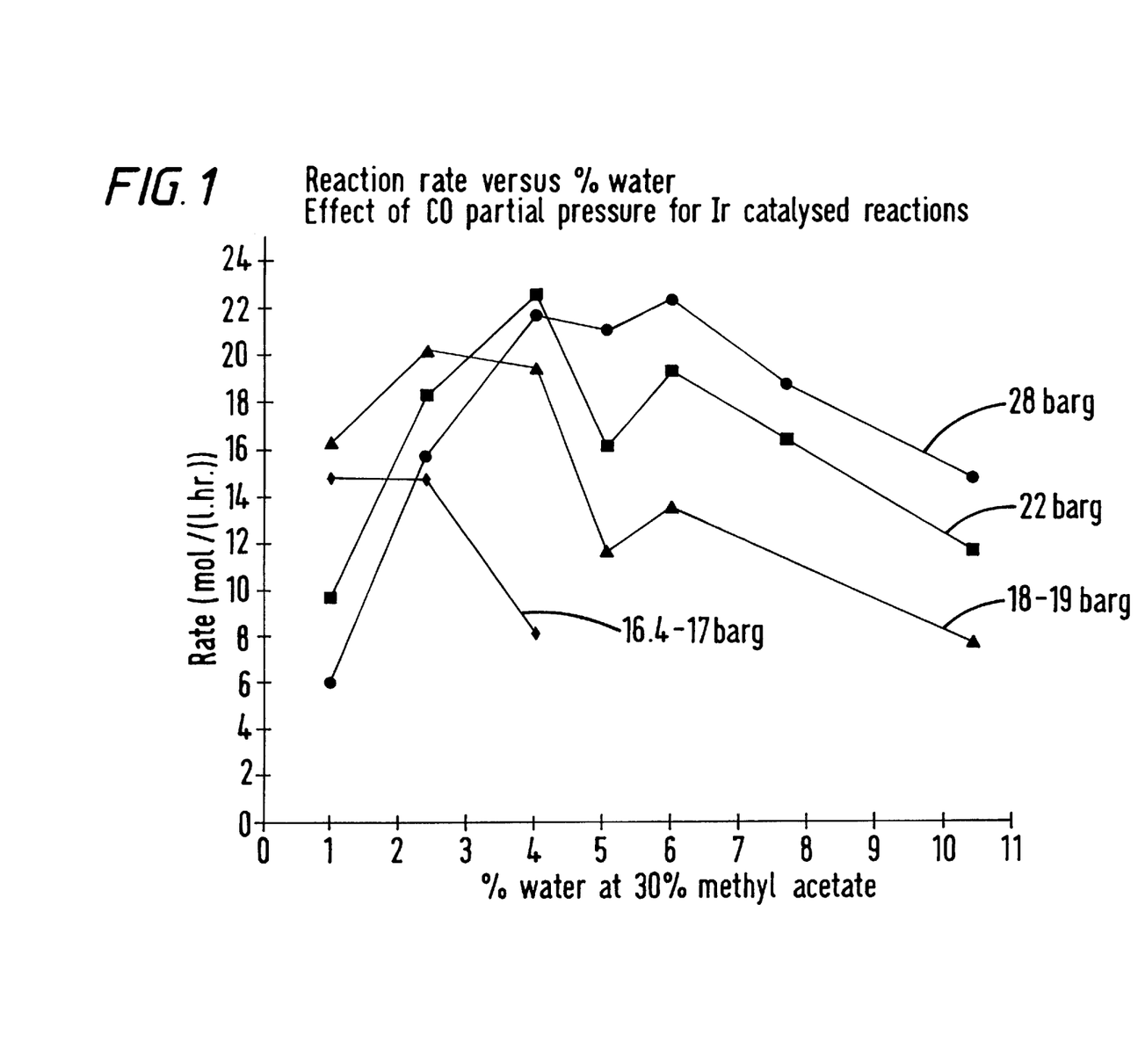
FIG. 1 is a plot of reaction rate versus % water at 30% methyl acetate—effect of CO partial pressure for unpromoted IR-catalyzed reactions.
Figure 2:
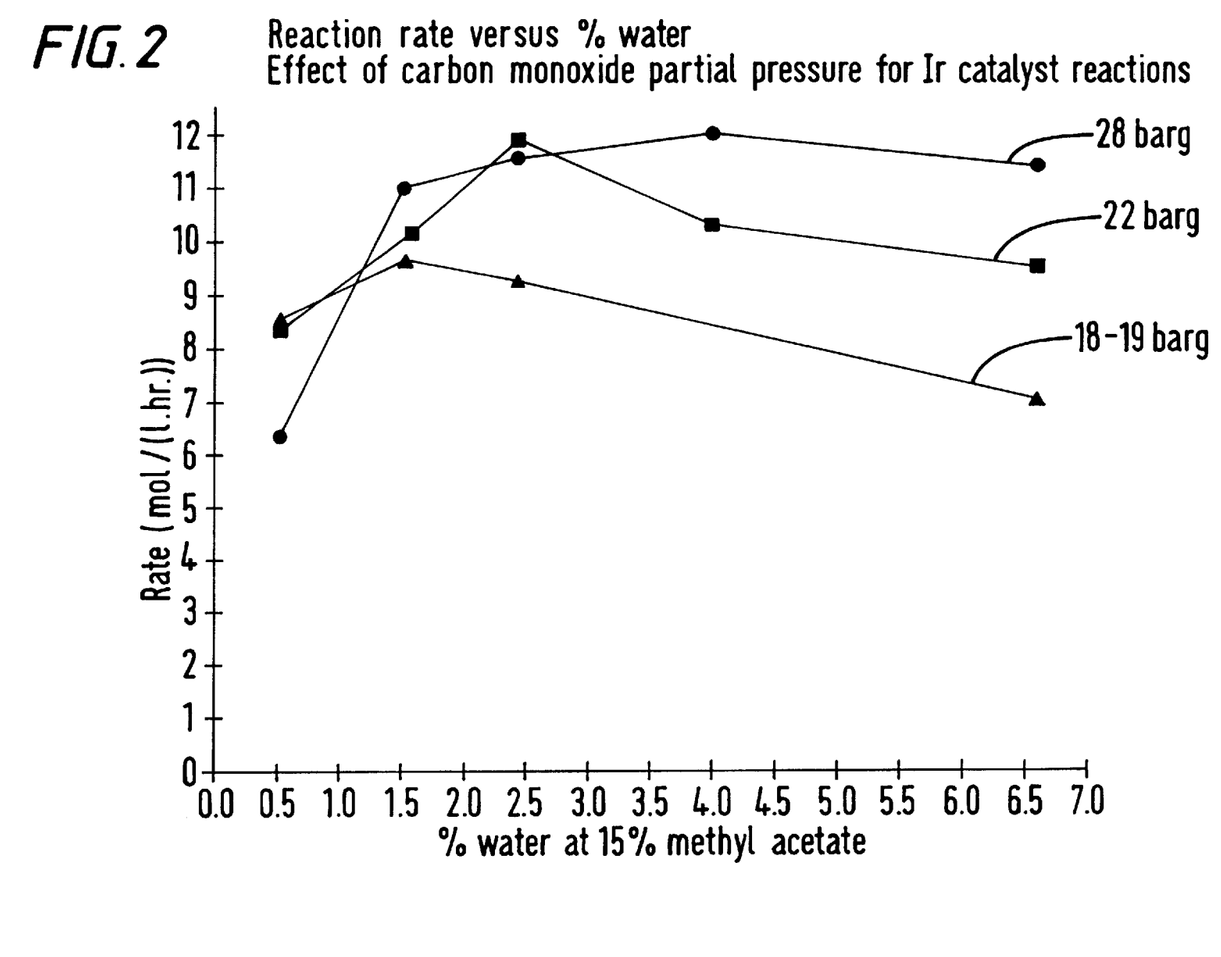
FIG. 2 is a plot of reaction rate versus % water at 15% methyl acetate—effect of CO partial pressure for unpromoted IR-catalyzed reactions.

The results in FIGS. 1 and 2 show that at 30 and 15% methyl acetate concentration in the reaction composition respectively for the un-promoted carbonylation, as total pressure, and hence carbon monoxide partial pressure, is reduced, the reaction rate maxima for the graphs of rate versus water concentration move to lower water concentration.

Figure 3:
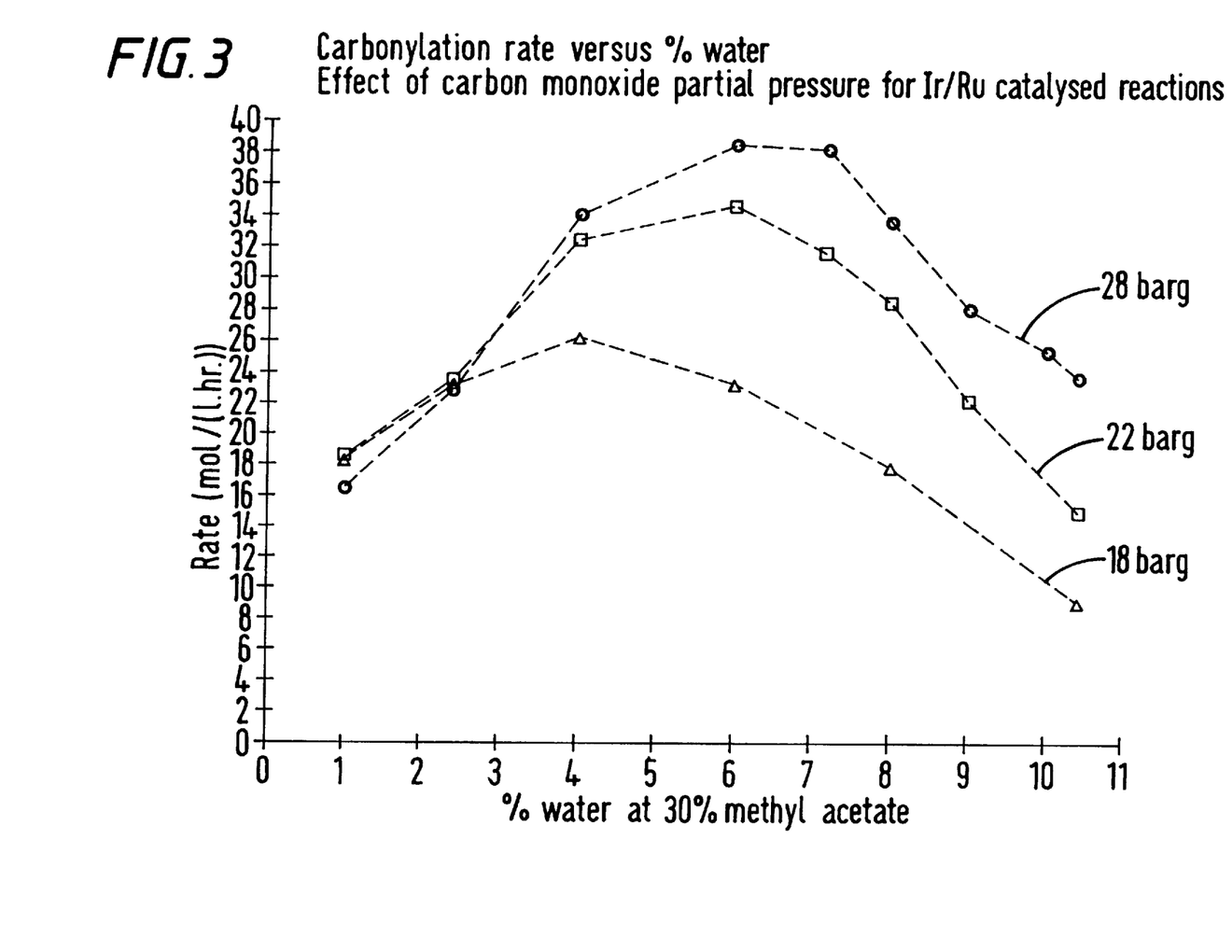
FIG. 3 is a plot of reaction rate versus % water at 30% methyl acetate—effect of CO partial pressure for ruthenium—promoted Ir-catalyzed reactions.
Figure 4:
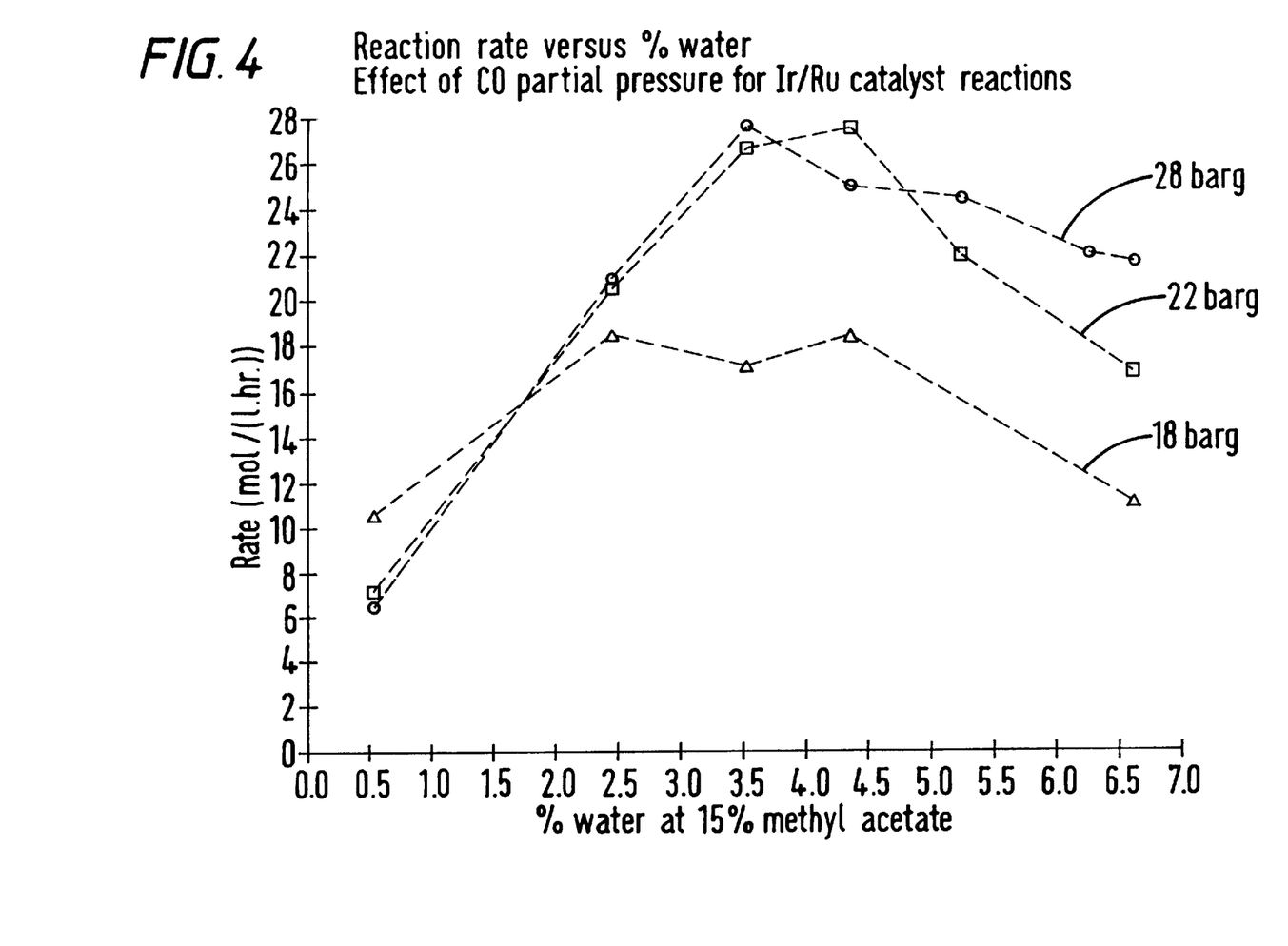
FIG. 4 is a plot of reaction rate versus % water at 15% methyl acetate—effect of CO partial pressure for ruthenium—promoted IR-catalyzed reactions.

The results in FIGS. 3 and 4, show the same effect as FIGS. 1 and 2 but for the ruthenium promoted system.

Figure 5:
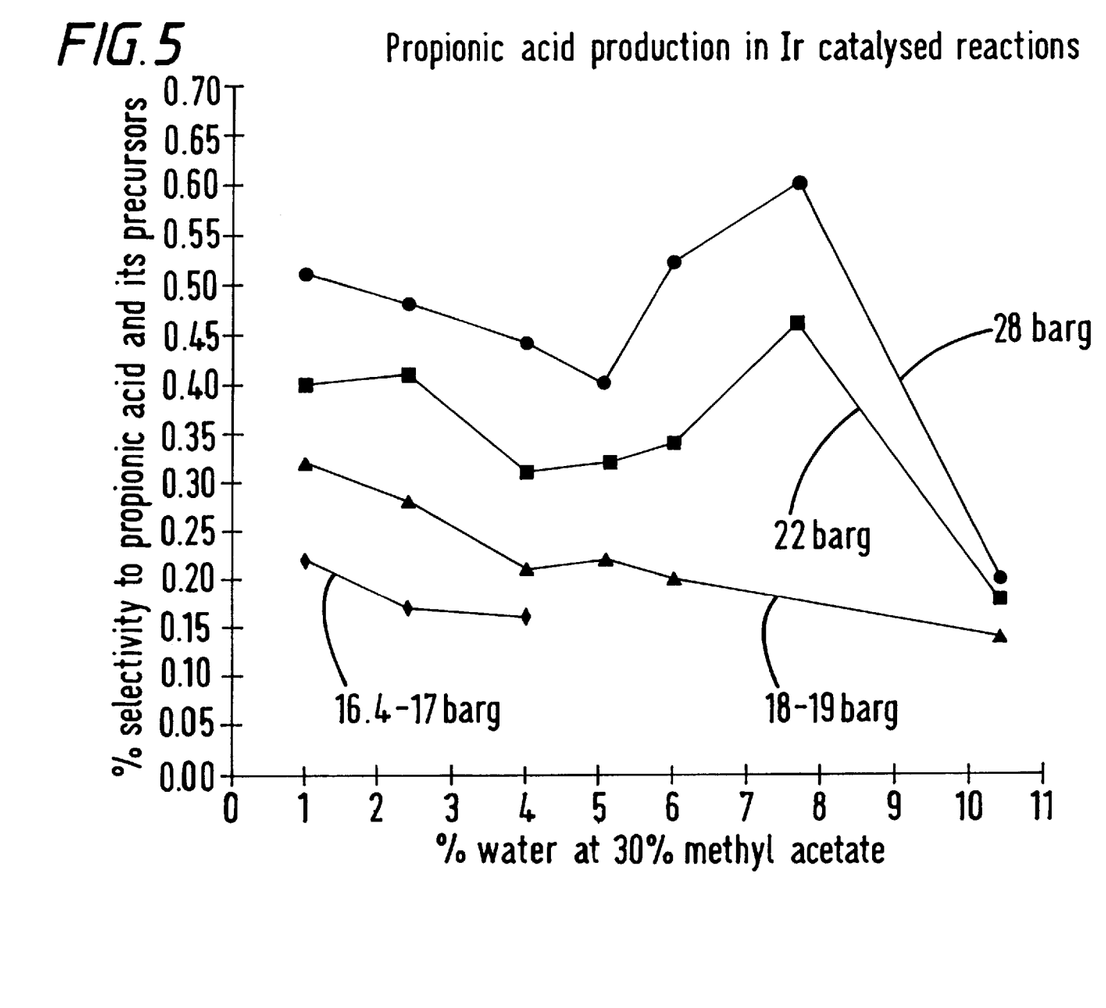
FIG. 5 is a plot of % selectivity to propionic acid and its precursors versus % water at 30% methyl acetate—effect of CO partial pressure for unpromoted Ir-catalyzed reaction.
Figure 6:
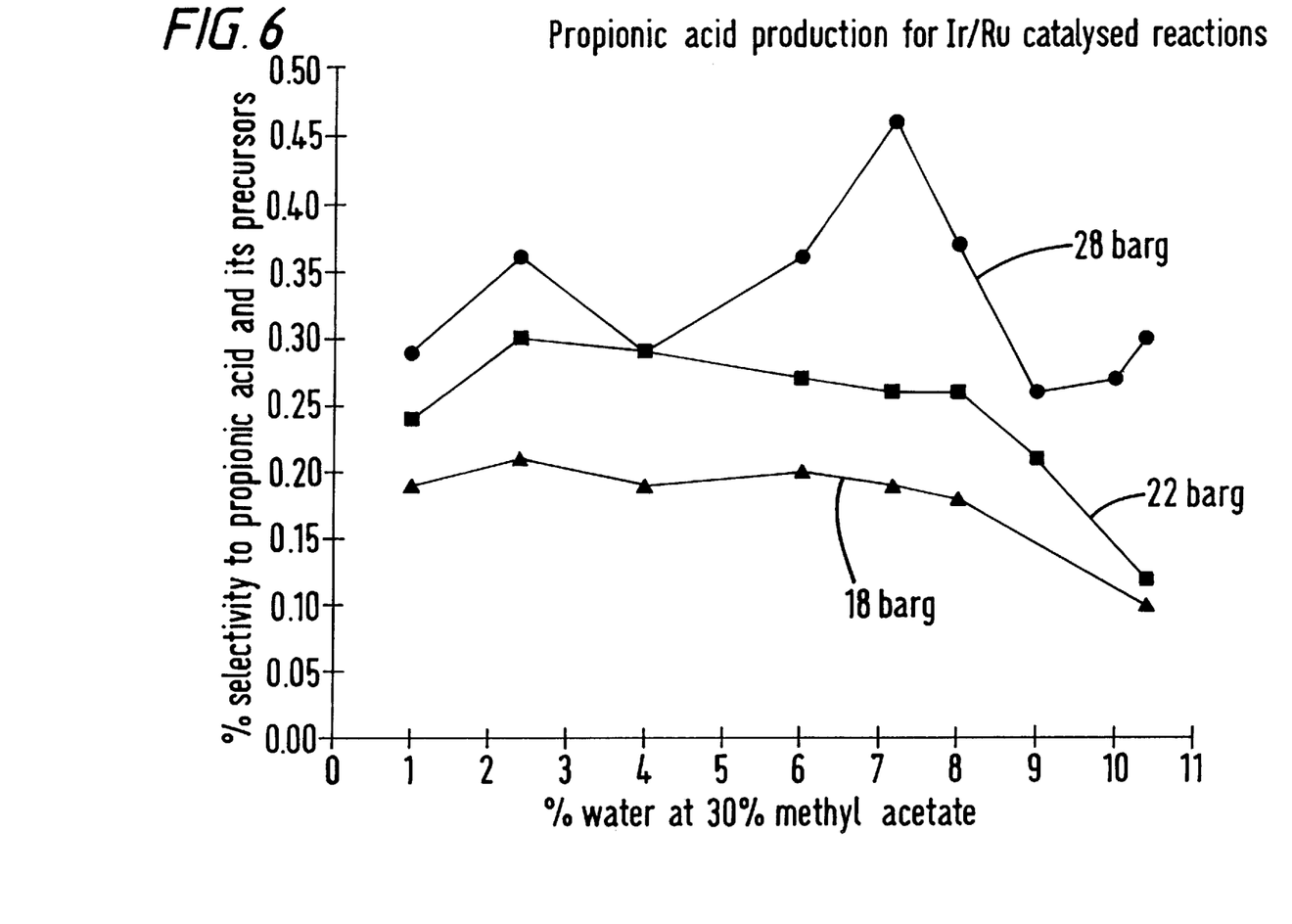
FIG. 6 is a plot of % selectivity to propionic acid and its precursors versus % water at 30% methyl acetate—effect of CO partial pressure of ruthenium—promoted iridium-catalyzed reactions.

The results in FIGS. 5 and 6 show the beneficial effect of reducing total pressure, and hence carbon monoxide partial pressure, on the formation of liquid by-products; propionic acid and its precursors ethyl iodide and ethyl acetate. Also in FIG. 3 the results show that at low water concentration (for example 1%) the reaction rate is almost independent of total pressure, and hence carbon monoxide partial pressure, which can be beneficial under conditions approaching total carbon monoxide consumption.

TABLE 1

| | Autoclave Charge | Main Charge | | | | Catalyst Injection $H_2IrCl_6$ | | |
|---|---|---|---|---|---|---|---|---|
| Run | AcOH | AcOH | MeOAc | $H_2O$ | MeI | Solution* | AcOH | $H_2O$ |
| 090596 | 11.21 | 53.38 | 60.09 | — | 13.36 | 1.30 | 6.50 | 4.21 |
| 090596A | 11.41 | 53.12 | 60.03 | — | 13.36 | 1.30 | 6.51 | 4.22 |
| 100596 | 12.71 | 51.78 | 60.00 | — | 13.33 | 1.31 | 6.50 | 4.24 |
| 130596 | 10.64 | 53.83 | 59.98 | — | 13.35 | 1.30 | 6.50 | 4.25 |
| 170596 | 11.77 | 54.08 | 60.05 | — | 13.36 | 1.31 | 5.13 | 4.22 |
| 210596A | 11.40 | 51.50 | 60.48 | 2.25 | 13.35 | 1.30 | 6.26 | 4.30 |
| 200596 | 10.02 | 52.63 | 60.40 | 2.25 | 13.32 | 1.31 | 6.50 | 4.31 |
| 170596A | 10.00 | 52.63 | 60.48 | 2.25 | 13.35 | 1.30 | 6.50 | 4.30 |
| 210596 | 10.15 | 52.63 | 60.48 | 2.25 | 13.34 | 1.31 | 6.50 | 4.30 |
| 150596 | 9.51 | 50.64 | 60.06 | 3.96 | 13.36 | 1.30 | 6.51 | 5.00 |
| 140596 | 7.15 | 53.03 | 60.00 | 3.96 | 13.32 | 1.30 | 6.50 | 5.00 |
| 160596 | 7.58 | 52.55 | 59.90 | 3.96 | 13.35 | 1.30 | 6.52 | 5.01 |
| 170696 | 9.51 | 50.64 | 50.99 | 3.96 | 13.36 | 1.30 | 6.50 | 5.00 |
| 060896 | 10.00 | 47.30 | 60.52 | 6.16 | 13.37 | 1.30 | 7.00 | 4.52 |
| 120896 | 9.99 | 47.30 | 60.51 | 6.24 | 13.43 | 1.31 | 7.00 | 4.55 |
| 130896 | 9.99 | 47.34 | 60.52 | 6.19 | 13.37 | 1.30 | 6.99 | 4.51 |
| 030796 | 10.00 | 46.34 | 60.00 | 7.55 | 13.39 | 1.30 | 7.00 | 4.50 |
| 040796 | 10.00 | 46.37 | 60.05 | 7.55 | 13.38 | 1.30 | 7.00 | 4.50 |
| 170796 | 10.02 | 46.37 | 60.04 | 7.56 | 13.38 | 1.31 | 7.00 | 4.50 |
| 250796 | 10.07 | 43.30 | 60.50 | 10.24 | 13.42 | 1.31 | 7.02 | 4.50 |
| 260796 | 10.05 | 43.30 | 60.50 | 10.23 | 13.42 | 1.31 | 7.00 | 4.50 |
| 230596 | 10.03 | 39.07 | 60.52 | 14.51 | 13.38 | 1.30 | 7.00 | 4.51 |
| 050696 | 10.10 | 39.99 | 60.48 | 14.51 | 13.38 | 1.31 | 7.00 | 4.50 |
| 140696 | 10.00 | 39.52 | 60.47 | 13.90 | 13.37 | 1.30 | 7.00 | 4.50 |

| | Autoclave Charges | | Main Charges | | | Catalyst Injection | | |
|---|---|---|---|---|---|---|---|---|
| Run | AcOH | $Ru(CO)_4I_2$ | AcOH | MeOAc | $H_2O$ | MeI | $H_2IrCl_6$ | AcOH | $H_2O$ |
| 270696 | 11.02 | 1.69 | 51.72 | 60.03 | — | 13.37 | 1.31 | 6.50 | 4.26 |
| 260696 | 11.00 | 1.69 | 51.76 | 60.00 | — | 13.36 | 1.31 | 6.50 | 4.26 |
| 280696 | 13.60 | 1.69 | 49.13 | 60.12 | — | 13.36 | 1.31 | 6.52 | 4.28 |
| 040696 | 10.01 | 1.69 | 51.00 | 60.50 | 2.26 | 13.36 | 1.31 | 6.50 | 4.30 |
| 030696 | 10.01 | 1.69 | 51.51 | 60.48 | 2.26 | 13.30 | 1.30 | 5.94 | 4.30 |
| 300596 | 10.15 | 1.69 | 51.24 | 60.48 | 2.26 | 13.34 | 1.30 | 6.02 | 4.29 |
| 120696 | 7.15 | 1.69 | 51.34 | 00.03 | 3.96 | 13.40 | 1.30 | 6.50 | 5.00 |
| 070696 | 7.15 | 1.69 | 51.34 | 60.05 | 3.96 | 13.39 | 1.30 | 6.50 | 5.01 |
| 110696 | 7.15 | 1.69 | 51.37 | 60.05 | 3.98 | 13.34 | 1.34 | 6.50 | 5.00 |
| 020796 | 13.63 | 1.69 | 45.38 | 60.43 | 7.37 | 13.66 | 1.31 | 4.15 | 4.76 |
| 050796 | 10.02 | 1.69 | 44.68 | 60.00 | 7.54 | 13.39 | 1.30 | 7.00 | 4.50 |
| 080796 | 10.02 | 1.69 | 44.72 | 60.00 | 7.55 | 13.40 | 1.31 | 7.00 | 4.51 |
| 140896 | 9.99 | 1.69 | 42.55 | 60.51 | 9.46 | 13.35 | 1.31 | 7.05 | 4.53 |
| 190796 | 10.05 | 1.69 | 42.48 | 60.50 | 9.44 | 13.34 | 1.30 | 7.01 | 4.50 |
| 160896 | 9.99 | 1.69 | 42.49 | 60.51 | 9.42 | 13.30 | 1.31 | 7.02 | 4.52 |
| 120796 | 10.05 | 1.69 | 40.95 | 60.50 | 10.81 | 13.41 | 1.31 | 7.01 | 4.50 |
| 090796 | 10.06 | 1.69 | 40.92 | 60.49 | 10.80 | 13.40 | 1.31 | 7.00 | 4.50 |

TABLE 1-continued

Reaction Compositions (Weights in Grams)

| | | | | | | | | | |
|---|---|---|---|---|---|---|---|---|---|
| 180796 | 10.05 | 1.69 | 40.95 | 60.60 | 10.81 | 13.42 | 1.31 | 7.03 | 4.50 |
| 110796 | 10.05 | 1.69 | 39.35 | 60.50 | 12.31 | 13.44 | 1.32 | 7.01 | 4.50 |
| 150796 | 10.05 | 1.69 | 39.95 | 60.50 | 12.31 | 13.45 | 1.32 | 7.02 | 4.50 |
| 240796 | 10.00 | 1.69 | 39.94 | 60.50 | 12.41 | 13.38 | 1.31 | 7.00 | 4.41 |
| 180696 | 10.55 | 1.69 | 39.52 | 60.47 | 13.91 | 13.36 | 1.31 | 5.31 | 4.50 |
| 160796 | 10.50 | 1.69 | 38.42 | 60.49 | 14.50 | 13.36 | 1.31 | 5.31 | 4.51 |
| 200696 | 19.9 | 1.69 | 29.40 | 60.53 | 14.71 | 13.33 | 1.30 | 6.00 | 4.60 |
| 210696 | 10.02 | 1.69 | 38.29 | 60.48 | 14.50 | 13.35 | 1.30 | 7.00 | 4.50 |

*$H_2IrCl_6$ solution in water contains 24.39% Ir

TABLE 2

| | Reaction Pressure (barg) | Rate (mol/l.hr.)) @ 30% MeOAc | Rate (mol/l.hr.) @ 15% MeOAc | % selectivity to propionic acid and its precursors* |
|---|---|---|---|---|
| Ir Only Experiments | | | | |
| 1% w/w water at 30% MeOAc, 8% MeI | | | | |
| 090596 | 28 | 6.01 | | 0.48 |
| 090596A | 28 | 5.91 | | 0.51 |
| 100596 | 22 | 9.69 | | 0.40 |
| 130596 | 18.2 | 16.33 | | 0.32 |
| 170596 | 16.4 | 14.83 | | 0.22 |
| 2.4% w/w water at 30% MeOAc, 8% MeI | | | | |
| 210596A | 28 | 15.72 | | 0.48 |
| 200595 | 22 | 18.25 | | 0.41 |
| 170596A | 18.1 | 20.18 | | 0.28 |
| 210596 | 17.0 | 14.75 | | 0.17 |
| 4% w/w water at 30% MeOAc, 8% MeI | | | | |
| 0.5% w/w water at 15% MeOAc | | | | |
| 150596 | 28 | 21.66 | 6.32 | 0.44 |
| 140596 | 22 | 22.53 | 8.34 | 0.31 |
| 160596 | 18.5 | 19.40 | 7.59 | 0.21 |
| 170696 | 16.8 | 8.11 | 4.88 | 0.16 |
| 5.1% w/w water at 30% MeOAc, 8% MeI | | | | |
| 1.55% w/w water at 15% MeOAc | | | | |
| 060896 | 28 | 20.99 | 10.28 | 0.40 |
| 120896 | 22 | 16.13 | 10.13 | 0.32 |
| 130896 | 18 | 11.62 | 9.63 | 0.22 |
| 6% w/w water at 30% MeOAc, 8% MeI | | | | |
| 2.4% w/w water at 15% MeOAc | | | | |
| 030796 | 28 | 22.32 | 11.52 | 0.52 |
| 040796 | 22 | 19.26 | 11.87 | 0.34 |
| 170796 | 18 | 13.56 | 9.24 | 0.20 |
| 7.7% w/w water at 30% MeOAc, 8% MeI | | | | |
| 4.0% w/w water at 30% MeOAc | | | | |
| 250796 | 28 | 18.73 | 11.98 | 0.60 |
| 260796 | 22 | 16.40 | 10.64 | 0.46 |
| 10.4% w/w water at 30% MeOAc, 8% MeI | | | | |
| 6.6% w/w water at 15% MeOAc | | | | |
| 230596 | 28 | 14.83 | 11.38 | 0.20 |
| 050696 | 22 | 11.68 | 9.49 | 0.18 |
| 140696 | 19 | 7.74 | 7.03 | 0.14 |
| Ir/Ru Experiments | | | | |
| 1% w/w water at 30% MeOAc, 8% MeI | | | | |
| 270696 | 28 | 16.50 | | 0.29 |
| 260696 | 22 | 18.58 | | 0.24 |
| 280696 | 18.0 | 18.38 | | 0.19 |
| 2.4% w/w water at 30% MeOAc, 8% MeI | | | | |
| 040696 | 28 | 22.83 | | 0.36 |
| 030696 | 22 | 23.54 | | 0.30 |
| 300596 | 18.0 | 22.00 | | 0.21 |
| 310596 | 18.0 | 23.19 | | 0.21 |
| 4% w/w water at 30% MeOAc, 8% MeI | | | | |
| 0.5% w/w water at 15% MeOAc, 7.6% MeI | | | | |
| 120696 | 28 | 33.54 | 6.44 | 0.29 |
| 070696 | 29 | 32.39 | 7.19 | 0.29 |
| 110696 | 18.2 | 26.21 | 10.64 | 0.19 |
| 6% w/w water at 30% MeOAc, 8% MeI | | | | |
| 2.4% w/w water at 15% MeOAc, 7.6% MeI | | | | |
| 020796 | 28 | 38.47 | 20.93 | 0.36 |
| 050796 | 22 | 34.61 | 20.50 | 0.27 |
| 080796 | 18 | 23.29 | 18.48 | 0.20 |
| 7.2% w/w water at 30% MeOAc, 8% MeI | | | | |
| 3.5% w/w water at 15% MeOAc, 7.6.% MeI | | | | |
| 140896 | 28 | 38.23 | 27.61 | 0.46 |
| 190796 | 22 | 31.65 | 26.59 | 0.26 |
| 160896 | 18 | 16.91 | 17.09 | 0.19 |
| 8% w/w water at 30% MeOAc, 8% MeI | | | | |
| 4.4% w/w water at 15% MeOAc, 7.6% MeI | | | | |
| 120796 | 28 | 33.64 | 24.97 | 0.41 |
| 090796 | 22 | 28.46 | 27.51 | 0.26 |
| 180796 | 18 | 17.91 | 18.38 | 0.18 |
| 9% w/w water at 30% MeOAc, 8% MeI | | | | |
| 5.2% w/w water at 15% MeOAc, 7.6% MeI | | | | |
| 110796 | 28 | 28.08 | 24.47 | 0.26 |
| 150796 | 28 | 27.74 | 21.68 | 0.37 |
| 240796 | 22 | 22.26 | 21.93 | 0.21 |
| 10.0% w/w water at 30% MeOAc, 8% MeI | | | | |
| 6.3% w/w water at 15% MeOAc, 7.6% MeI | | | | |
| 180696 | 28 | 25.40 | 22.03 | 0.27 |
| 10.4% w/w water at 30% MeOAc, 8% MeI | | | | |
| 6.6% w/w water at 15% MeOAc, 7.6% MeI | | | | |
| 160796 | 28 | 23.77 | 21.65 | 0.30 |
| 200696 | 22 | 15.08 | 16.86 | 0.12 |
| 210696 | 18.0 | 9.18 | 11.20 | 0.10 |

(*Based on MeOAc consumed. Precursors are ethyl iodide and ethyl acetate)

We claim:

1. Process for the production of acetic acid which process comprises (1) continuously feeding methanol and/or a reactive derivative thereof and carbon monoxide to a carbonylation reactor containing a liquid reaction composition comprising an iridium carbonylation catalyst, methyl iodide co-catalyst, a finite concentration of water, acetic acid, methyl acetate and, optionally at least one promoter; (2) carbonylating the methanol and/or reactive derivative thereof with the carbon monoxide in the liquid reaction composition to produce acetic acid; and (3) recovering acetic acid from the liquid reaction composition, there being continuously maintained (a) in the liquid reaction composition water at a concentration of no greater than 4.5% by weight, and (b) in the reactor a carbon monoxide partial pressure in the range from greater than 0 to 7.5 bar.

2. A process as claimed in claim 1 in which there is continuously maintained in the liquid reaction composition throughout the course of the reaction a water concentration of no greater than 3% by weight.

3. A process as claimed in claim 1 in which there is continuously maintained in the liquid reaction composition throughout the course of the reaction a water concentration of at least 0.1% by weight.

4. A process as claimed in claim 1 in which there is continuously maintained in the liquid reaction composition throughout the course of the reaction a water concentration of at least 0.5% by weight.

5. A process as claimed in claim 1 in which there is continuously maintained in the liquid reaction composition throughout the course of the reaction methyl acetate at a concentration in the range 2 to 50% by weight.

6. A process as claimed in claim 5 in which there is continuously maintained in the liquid reaction composition throughout the course of the reaction methyl acetate at a concentration in the range 5 to 50% by weight.

7. A process as claimed in claim 5 in which there is continuously maintained in the liquid reaction composition throughout the course of the reaction methyl acetate at a concentration in the range 5 to 40% by weight.

8. A process as claimed in claim 5 in which there is continuously maintained in the liquid reaction composition throughout the course of the reaction methyl acetate at a concentration in the range 10 to 40% by weight.

9. A process as claimed in claim 1 in which there is continuously maintained in the liquid reaction composition throughout the course of the reaction methyl iodide at a concentration in the range 4 to 16% by weight.

10. A process as claimed in claim 1 wherein the iridium carbonylation catalyst is present in the liquid reaction composition at a concentration in the range 400 to 5000 ppm.

11. A process as claimed in claim 1 wherein the iridium carbonylation catalyst is present in the liquid reaction composition at a concentration in the range 700 to 3000 ppm.

12. A process as claimed in claim 1 in which the at least one promoter is selected from the group consisting of ruthenium, osmium, rhenium, and tungsten.

13. A process as claimed in claim 11 in which the molar ratio of promoter:iridium is 0.5:1 to 15:1.

14. A process as claimed in claim 1 in which there is continuously maintained in the reactor throughout the course of the reaction a carbon monoxide partial pressure in the range 0.6 to 7.5 bar.

15. A process as claimed in claim 1 in which there is continuously maintained in the reactor throughout the course of the reaction a hydrogen partial pressure of less than 0.3 bar.

16. A process as claimed in claim 1 in which there is continuously maintained in the liquid reaction composition throughout the course of the reaction about 0.5 to 2.5% by weight water, about 8% by weight methyl iodide co-catalyst, about 15% methyl acetate, iridium catalyst at a cencentration in the range 400 to 3000 ppm, ruthenium promoter at a concentration in the range 400 to 4000 ppm and the balance of the reaction composition comprising substantially acetic acid.

* * * * *